(12) United States Patent
Kageyama et al.

(10) Patent No.: US 8,059,270 B2
(45) Date of Patent: Nov. 15, 2011

(54) MICROCHIP

(75) Inventors: Yasuhisa Kageyama, Kyoto (JP); Toshihiro Mori, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 343 days.

(21) Appl. No.: 12/276,685

(22) Filed: Nov. 24, 2008

(65) Prior Publication Data

US 2009/0135407 A1 May 28, 2009

(30) Foreign Application Priority Data

Nov. 26, 2007 (JP) .................................. 2007-304509

(51) Int. Cl.
*G01N 21/01* (2006.01)
(52) U.S. Cl. ........................................................ 356/244
(58) Field of Classification Search .................. None
See application file for complete search history.

(56) References Cited

U.S. PATENT DOCUMENTS

| | | | |
|---|---|---|---|
| 6,033,628 A * | 3/2000 | Kaltenbach et al. ......... | 422/68.1 |
| 2008/0156079 A1 | 7/2008 | Momose et al. | |
| 2008/0296734 A1 | 12/2008 | Momose | |
| 2009/0084738 A1 | 4/2009 | Momose | |
| 2009/0098658 A1 | 4/2009 | Momose et al. | |
| 2009/0104077 A1 | 4/2009 | Momose | |
| 2009/0111675 A1 | 4/2009 | Yokogawa et al. | |
| 2009/0142232 A1 | 6/2009 | Okada et al. | |
| 2009/0155125 A1 | 6/2009 | Michiue et al. | |
| 2009/0232708 A1 | 9/2009 | Yokogawa et al. | |

FOREIGN PATENT DOCUMENTS

JP  2007-017342  1/2007

OTHER PUBLICATIONS

U.S. Appl. No. 12/467,404, filed May 18, 2009.
U.S. Appl. No. 12/424,913, filed Apr. 16, 2009.

* cited by examiner

*Primary Examiner* — Tu Nguyen
(74) *Attorney, Agent, or Firm* — Fish & Richardson P.C.

(57) ABSTRACT

There is provided a microchip that is formed of a first substrate having a surface with a groove and a second substrate joined together and has a fluid circuit in the form of a cavity defined by the groove and a surface of the second substrate closer to the first substrate. The fluid circuit at least includes a detection portion having an optical path for transmitting light. The microchip includes at least one of a step defined by a groove formed in contact with at least one side surface of a groove of the first substrate that defines the optical path and a recess provided in the second substrate at a position opposite to the step.

10 Claims, 3 Drawing Sheets

MICROCHIP

BACKGROUND OF THE INVENTION

1. Field of the Invention

The present invention relates generally to microchips useful as a micro total analysis system (μ-TAS) or the like suitably used for biochemical test of DNA, protein, cell, immunity, blood and the like, chemical synthesis and environmental analysis and the like, and particularly to microchips having a detection portion for optical measurement.

2. Description of the Background Art

In recent years in the fields of medical care, health, food, medicine development and the like it has been increasingly important to sense, detect or assay deoxyribo nucleic acid (DNA), enzymes, antigen, antibody, protein, viruses, cells and other similar biological substances and chemical substances, and there have been proposed a variety of biochips and micro chemical chips that can measure such substances conveniently. (Hereinafter such chips will be referred to as a "microchip" collectively.)

The microchip allows a series of test and analysis operations that are conducted in a laboratory to be conducted within a chip of a square measuring a few centimeters to 10 cm per side and having a thickness of approximately a few millimeters to a few centimeters. It thus allows the test and analysis operations to be conducted with a small amount of specimen and reagent, at a reduced cost, and with quick response and high throughput, and thus has many advantages such as a test result obtained immediately at a site at which the specimen is obtained.

Normally, the microchip has a fluid circuit therein. The fluid circuit is configured mainly e.g., of a liquid reagent reservoir portion for reserving a liquid reagent to be mixed with or used to cause a reaction with a specimen (e.g., blood as an example thereof) or used to treat the specimen, a measurement portion for measuring the specimen, the liquid reagent and the like, a mixer portion for mixing the specimen and the liquid reagent together to obtain a liquid mixture thereof, a detection portion for analyzing and/or testing the obtained liquid mixture and other similar portions, and a small flow path (e.g., having a width of approximately a few hundreds μm) connecting these portions appropriately. For use, the microchip is mounted typically in a device (a centrifuge) that can apply centrifugal force thereto. The microchip with appropriately directed centrifugal force applied thereto allows a specimen and a liquid reagent to be measured in amount and mixed together to provide a liquid mixture thereof and the liquid mixture to be introduced into the detection portion and the like. (For example see Japanese Patent Laying-open No. 2007-017342 for an example of a microchip having a fluid circuit therein.)

The detection portion having the liquid mixture accommodated therein is for example exposed to light (for detection) to measure the liquid mixture in transmittance or subject it to similar optical measurement.

SUMMARY OF THE INVENTION

A microchip having a fluid circuit therein can be fabricated by joining a first substrate having one surface with a groove and a second substrate together such that the first substrate has the grooved surface opposite to the second substrate. The substrates can be joined together for example by melting with a laser or the like a surface of at least one substrate that is joined to the other, and thus welding the substrates together.

If the microchip is fabricated by welding the substrates together, a substrate that is melted is often raised in joining the substrates together. If the substrate is raised in the fluid circuit at the detection portion, the raised substrate interrupts a portion of an optical path (i.e., a cavity provided in the detection portion to pass light therethrough for detection) and thus makes it difficult to conduct optical measurement.

However, avoiding such interruption of the optical path by increasing the optical path in length in the microchip's depthwise direction requires a test/analysis to be conducted with an increased amount of a specimen and an increased amount of a liquid reagent, and the microchip's advantage cannot be maximally utilized.

The present invention has been made to overcome the above disadvantage, and it contemplates a microchip including a detection portion that can prevent a substrate melted to be joined to another substrate from interrupting an optical path, and can thus ensure reliable optical measurement.

More specifically the present invention relates to a microchip formed of a first substrate having a surface with a groove and a second substrate joined together, and having a fluid circuit in a form of a cavity defined by the groove and a surface of the second substrate closer to the first substrate. The fluid circuit at least includes a detection portion having an optical path for transmitting light, and the microchip includes at least one of a step defined by a groove formed in contact with at least one side surface of a groove of the first substrate that defines the optical path and a recess provided in the second substrate at a position opposite to the step.

Herein in the present invention preferably the first substrate at least has two steps formed in contact with two side surfaces of the groove defining the optical path. More preferably, the two side surfaces of the groove defining the optical path are a plane of incidence of the light and a plane of emission of the light.

In the present invention in one preferable embodiment the first substrate has the step and the second substrate does not have the recess.

Preferably, the groove defining the optical path has a depth of at least 1 mm and at most 2 mm. Furthermore, preferably, the groove defining the step has a depth of at most 0.5 mm and more preferably a depth of at most 0.1 mm.

In the present invention, the first substrate is preferably a transparent substrate. The second substrate is preferably an opaque substrate, more preferably a black substrate.

The present invention can effectively reduce or prevent the interruption of an optical path that is caused by a substrate melted to be joined to another substrate. A microchip can thus be provided that includes a detection portion that ensures reliable optical measurement.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
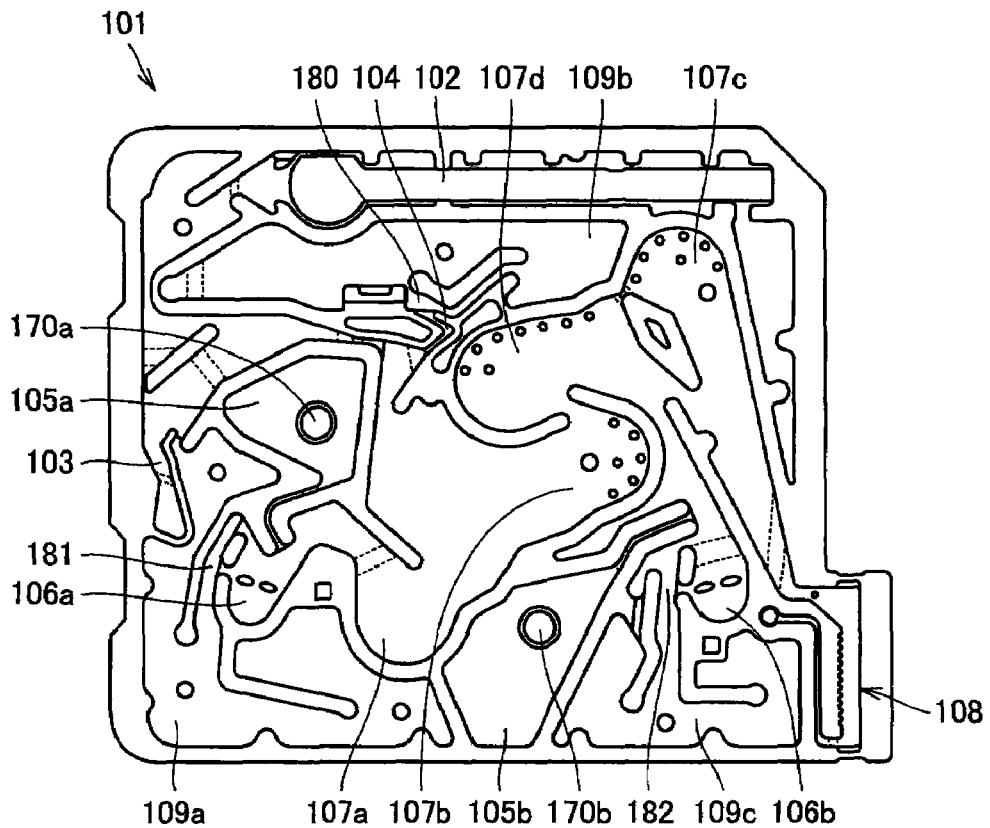
FIG. 1 is a schematic top view of a grooved surface of a first substrate configuring a microchip of one preferable embodiment of the present invention.

The present microchip is a microchip having a fluid circuit in an interior configured of a first substrate having a grooved surface and a second substrate joined on the grooved surface of the first substrate. The fluid circuit is in the form of a cavity defined by a groove formed in a surface of the first substrate and a surface of the second substrate that is joined to the first substrate (i.e., a surface of the second substrate closer to the first substrate). The microchip is not limited to a particular size. It can for example have a length of approximately a few centimeters, a width of approximately a few centimeters, and a thickness of approximately a few millimeters to approximately 1 cm.

In the present invention the first and second substrates can be formed of a variety of resins (such as thermoplastic resin). Furthermore, the groove formed in a surface of the first substrate is not limited to any particular geometry or pattern; it is determined to allow the groove and the second substrate's surface to configure a cavity having a structure to be that of an appropriate fluid circuit as desired.

In the present microchip the fluid circuit has a variety of portions in the fluid circuit at appropriate positions to subject fluid (liquid in particular) in the fluid circuit to a variety of appropriate treatments, and these portions are connected through a small flow path appropriately.

While the above portions are not particularly limited, they can include a liquid reagent reservoir portion for reserving a liquid reagent, a measurement portion for measuring a specimen (or a particular component therein, which will hereinafter also be simply referred to as a "specimen"), the liquid reagent and the like, a mixer portion for mixing the measured liquid reagent and the measured specimen together to obtain a liquid mixture thereof, a detection portion for conducting a test/analysis of the liquid mixture (e.g., detecting a particular component in the liquid mixture), and the like. If necessary, an additional portion may be provided. The measurement portion has a predetermined volume and can receive the specimen, the liquid reagent and the like therein to measure the specimen, the liquid reagent and the like by a predetermined amount. It should be noted that the liquid reagent is a reagent used to treat a specimen subjected to a test/analysis conducted with the microchip, or mixed with or caused to react with the specimen, and normally, it is incorporated in the fluid circuit at the liquid reagent reservoir portion previously before the microchip is used.

Measuring the specimen, liquid reagent and the like, mixing them together to obtain a liquid mixture thereof, introducing the liquid mixture into the detection portion, and other steps performed in the fluid circuit to treat fluid can be done by applying an appropriately directed centrifugal force in an order to the microchip, typically mounted in a device (a centrifuge) that can apply centrifugal force to the microchip.

The present microchip essentially includes the detection portion as a portion of its fluid circuit. The detection portion receives the liquid mixture or a similar substance to be measured and the detection portion is for example exposed to light to detect the transmitted light's intensity (or transmittance) and thus subject the liquid mixture or the similar substance to optical measurement to test/analyze the specimen.

Hereinafter, the present microchip will more specifically be described with reference to one preferable embodiment. FIG. 1 is a schematic top view of a grooved surface of a first substrate 101 configuring a microchip 100 of one preferable embodiment of the present invention. In the present embodiment microchip 100 is fabricated by welding and thus joining first substrate 101 at the grooved surface, as shown in FIG. 1, and a second substrate 301 (not shown in FIG. 1) together. Microchip 100 has a fluid circuit structure that can suitably be applied as a microchip extracting blood plasma from blood and conducting a test/analysis on the blood plasma.

With reference to FIG. 1, the fluid circuit that microchip 100 has is configured mainly of: a sampling tube mounting portion 102 for incorporating a sampling tube such as a capillary containing blood obtained from a subject; a blood plasma separation portion 103 removing blood cells and a similar component from the blood introduced from the sampling tube to obtain blood plasma; a specimen measurement portion 104 for measuring the separated blood plasma; two liquid reagent reservoir portions 105a and 105b for reserving a liquid reagent; liquid reagent measurement portions 106a and 106b for measuring two types of liquid reagents, respectively; mixer portions 107a, 107b, 107c and 107d for mixing the blood plasma and the liquid reagent together to obtain a liquid mixture thereof, and a detection portion 108 subjecting the liquid mixture to a test/analysis. Microchip 100 is a "liquid reagent incorporated microchip" having a liquid reagent previously incorporated in the fluid circuit. The liquid reagent is introduced from a surface of microchip 100 at first substrate 101 into liquid reagent reservoir portions 105a and 105b through liquid reagent introduction ports 170a, 170b provided in the form of a through hole penetrating first substrate 101 depthwise. These liquid reagent introduction ports have their respective openings sealed with a sealing label or the like placed on the surface of microchip 100 at first substrate 101.

Figure 2:
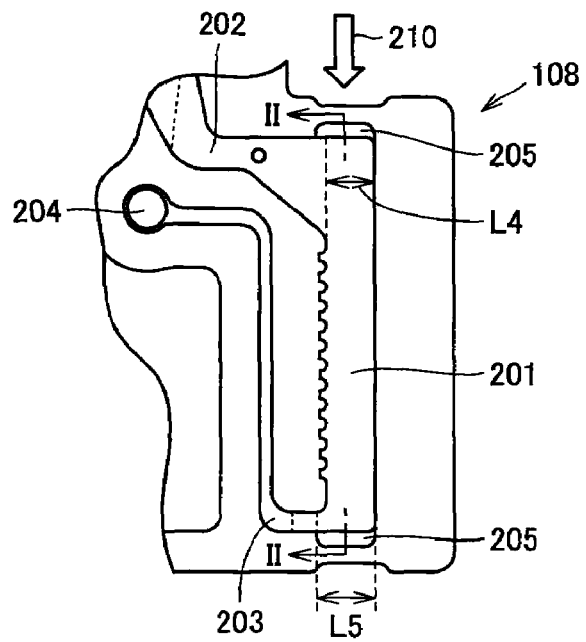
FIG. 2 is an enlarged top view of a detection portion of the microchip shown in FIG. 1.

FIG. 2 is an enlarged top view of detection portion 108 of microchip 100. Detection portion 108 has an optical path 201 generally in the form of a rectangular parallelepiped and passing therethrough light 210 radiated in optical measurement for detection. Optical path 201 has one end with an inlet flow path 202 for introducing the liquid mixture or a similar substance subjected to optical measurement. Optical path 201 has the other end connected through an outlet flow path 203 to an air vent 204. Air vent 204 is a through hole penetrating first substrate 101 depthwise.

Figure 3:
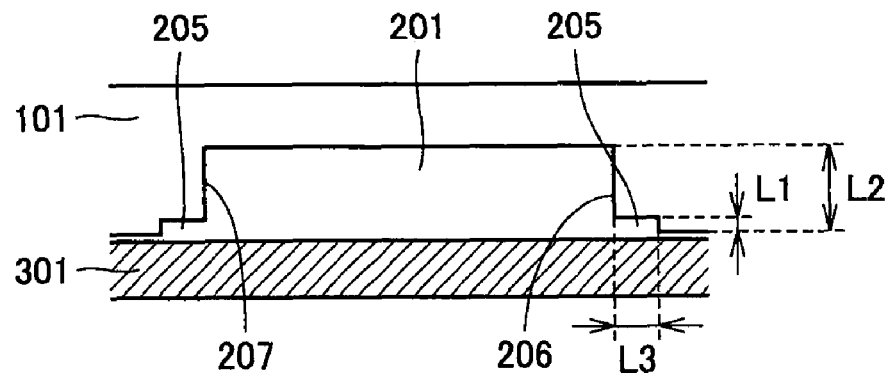
FIG. 3 is a cross section taken along a line II-II shown in FIG. 2.

FIG. 3 is a cross section taken along a line II-II shown in FIG. 2. FIG. 3 also shows second substrate 301 joined to first substrate 101. As shown in FIG. 3, optical path 201 is defined by a groove, which has a side surface in contact with two steps 205. Step 205 is defined by a groove formed at a surface of first substrate 101 in contact with the side surface of the groove defining optical path 201. The groove defining optical path 201 and that defining step 205 are different in depth, and optical path 201 thus has a side surface (a surface of first substrate 101) with a step.

Figure 4:
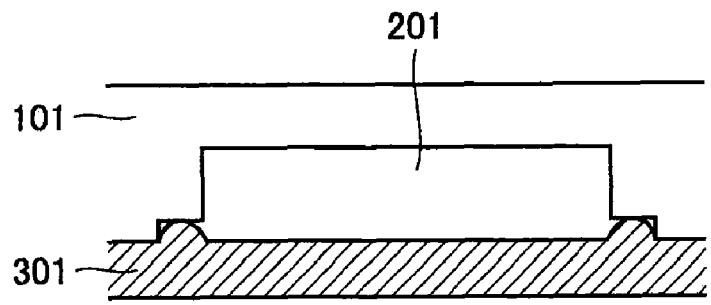
FIG. 4 is a schematic cross section of the FIG. 3 first and second substrates welded together with a laser.
Figure 5:
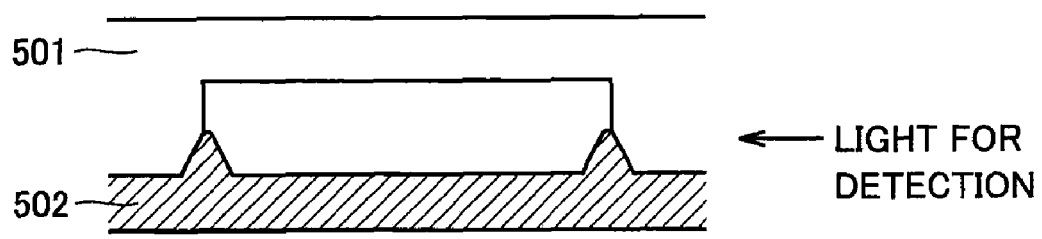
FIG. 5 is a schematic cross section of an optical path of a conventional microchip formed of a steeples first substrate and a second substrate welded together with a laser.

The side surface of the groove defining optical path 201 that is provided with step 205 is a plane of incidence 206 and a plane of emission 207 passing light 210 therethrough. Such step 205 forms a cavity in detection portion 108 for accommodating a substrate (second substrate 301 in particular) welding out in detection portion 108 when the substrate is welded. More specifically, by providing step 205, second substrate 301 welding out when first substrate 101 and second substrate 301 shown in FIG. 3 are welded together with a laser will be accommodated in a cavity defined by step 205 and a surface of second substrate 301 and coupled to optical path 201 (see FIG. 4). This can prevent a substrate welding out in joining it with another substrate from interrupting an optical path for light for detection. If such a stepped structure is absent, as shown in FIG. 5, a first substrate 501 and a second substrate 502 joined together occasionally has a substrate welding out and thus raised to interrupt an optical path for light for detection.

It is not a requirement to provide step 205 at both the plane of incidence of light for detection and the plane of emission of light for detection. To ensure an optical path for light for detection, however, it is preferable to provide it at both the plane of incidence and the plane of emission.

With reference to FIG. 3, it is necessary that step 205 has a depth L1 (a distance from the grooved surface of first substrate 101 to a surface of step 205) smaller than a depth L2 of the groove defining optical path 201. When the diameter of the spot of light used for detection, facilitating registering the light's optical axis and the plane of incidence 206, and the like are considered, the plane of incidence of the light for detection and the plane of emission of the light for detection preferably have a length (L2−L1) of approximately at least 1 mm. Furthermore, the groove defining optical path 201 has depth L2 preferably of at least 1 mm and at most 2 mm. L2 exceeding 2 mm requires introducing a substance to be measured into the detection portion in an increased amount, and the microchip's advantage cannot maximally be utilized. More preferably, L2 is at most 1.5 mm. Step 205 preferably has depth L1 determined with the above point as well as a substrate's volume welding out, and the like considered. Step 205 has depth L1 preferably of at most 0.5 mm, more preferably at most 0.1 mm. If step 205 has depth L1 exceeding 0.5 mm, a plane of incidence and a plane of emission that have a sufficient length may not be ensured. Step 205 has a widthwise length L3 (see FIG. 3), which is not particularly limited. Widthwise length L3 is determined, as appropriate, with a substrate's volume welding out and the like considered. Step 205 can have widthwise length L3 for example of approximately 0.1 to 0.5 mm.

With reference to FIG. 2, optical path 201 has a width L4, which is not particularly limited. When facilitating registering the optical axis of the light for detection and the optical path's plane of incidence 206, and the like are considered, however, it is preferable to set it at approximately at least 0.5 mm and approximately at most 2 mm, more preferably approximately at least 0.8 mm and approximately at most 1.5 mm. Step 205 has a length L5 in a direction parallel to width L4 of optical path 201. Length L5 is preferably equal to or larger than L4. More preferably, step 205 has width L5 larger than width L4 of optical path 201. In the FIG. 2 detection portion 108 step 205 extends into inlet flow path 202 and outlet flow path 203 in order to ensure that a substrate welding out is accommodated over the entirety of the plane of incidence of the light for detection and that of the plane of emission of the light for detection to ensure an optical path.

A substrate welding out may be accommodated in a cavity coupled to optical path 201 that is formed by providing together with or in place of the above described step a recess (or groove) provided in a surface of the second substrate that is joined to the first substrate. The recess provided in the second substrate at a surface is provided in the second substrate at least at a position opposite to the step to allow the recess and the surface of the first substrate that is joined to provide a cavity coupled to the optical path. In other words, the recess provided in the second substrate at a surface is provided in the second substrate at a surface that is joined to the first substrate at least at a region directly under a side surface of the groove defining the optical path provided to the first substrate.

Figure 6A:
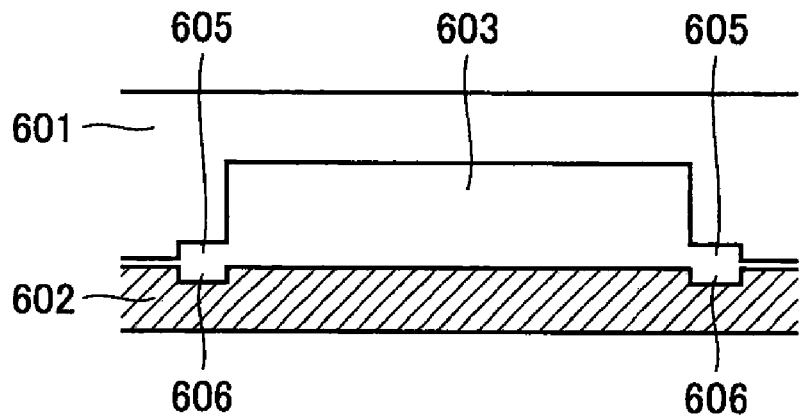
FIGS. 6A-6C are schematic cross sections of the detection portion according to the present invention in other examples.
Figure 6B:
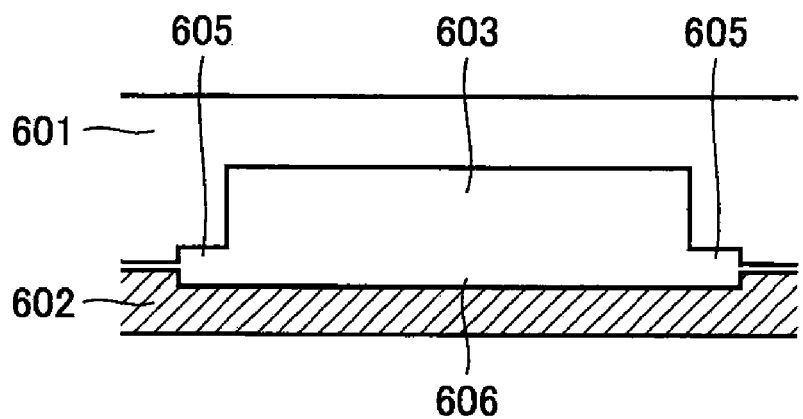
Figure 6C:
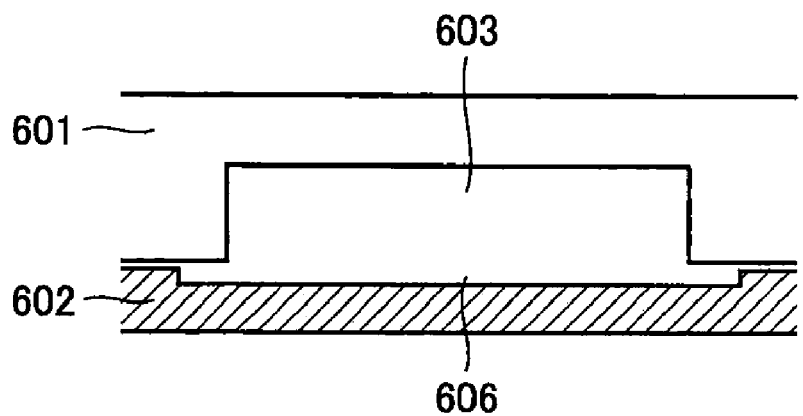

FIGS. 6A-6C are schematic cross sections of the detection portion according to the present invention in other examples. As shown in FIGS. 6A and 6B, a cavity formed to be coupled to an optical path 603 for accommodating a substrate welding out may be defined by a step 605 formed at a first substrate 601 and a recess 606 formed in a second substrate 602. Alternatively, the cavity may be defined by recess 606 alone that is formed in second substrate 602, as shown in FIG. 6C.

Of the above examples, it is particularly preferable to provide the cavity only by the step provided at the first substrate, as shown in FIG. 3. This configuration allows the cavity and furthermore, the entirety of the fluid circuit to be provided without providing the second substrate with a groove (a recess).

The first substrate (a substrate having formed therein a groove configuring a fluid circuit) and the second substrate that configure the present microchip are not limited to any particular material. When workability is considered, however, they are formed preferably of resin, polystyrene resin, cycloolefin polymer (COP), acrylic resin and the like in particular. Inter alia, polystyrene resin is more preferable as it is satisfactory in moisture resistance and workability (extrusion moldability).

In optical measurement the first substrate includes the plane of incidence and plane of emission of the optical path exposed to the light for detection. Accordingly, it is preferable that the first substrate be a transparent substrate and it is necessary that the detection portion has the optical path at least with the plane of incidence and the plane of emission configured of a transparent member (e.g., transparent resin). The second substrate may be a transparent substrate or an opaque substrate. When the first substrate and the second substrate are joined together, the substrates can be welded with a laser, thermally, ultrasonically or the like. For example if the substrates are welded with a laser, at least one of the substrates has a surface to be joined exposed to the laser and thus melted and thus bonded, and in doing so a substrate that is an opaque substrate (preferably a black substrate) allows an increased optical absorption rate and can be welded with the laser efficiently. Accordingly, if the first substrate is a transparent substrate, the second substrate that is an opaque substrate is preferable and the second substrate that is a black substrate is more preferable. If the first substrate and the second substrate are a transparent substrate and a black substrate, respectively, and formed of the same resin, and a laser is used to weld the substrates together, typically, the laser can be radiated to first pass through the first substrate to expose the substrates' respective surfaces to be joined to the laser to melt the second substrate's surface to be joined to bond the substrates together.

The step and/or second substrate's recess as described above may be provided not only in the detection portion but also another portion of the fluid circuit. Such a portion can include e.g., specimen measurement portion 104 for measuring blood plasma, liquid reagent measurement portions 106a and 106b for measuring a liquid reagent, and the like. Each measurement portion measures a predetermined amount of liquid and is accordingly required to have a predetermined volume. A measurement portion that has a step, a recess and/or the like can be prevented from having a volume reduced as a substrate is raised. Note that it is needless to say that in the present invention the fluid circuit is not limited in configuration to that shown in FIG. 1

Finally, a method of operating the FIG. 1 microchip 100 will be described in one example. Note that the below described method is merely exemplary and is not limitative.

Initially a sampling tube containing blood obtained from a subject is mounted in sampling tube mounting portion 102. Subsequently, centrifugal force is applied to microchip 100 leftward, as seen in FIG. 1, and the blood in the sampling tube is extracted, and subsequently, downward centrifugal force is applied to introduce the blood into blood plasma separation portion 103 to centrifugally separate the blood into blood plasma (an upper layer) and blood cells (a lower layer). In doing so, excessive blood is accommodated in a drainage reservoir 109a. Furthermore, the downward centrifugal force introduces a liquid reagent X that is reserved in liquid reagent reservoir portion 105a into liquid reagent measurement portion 106a for measurement. Liquid reagent X that spills over liquid reagent measurement portion 106a flows through a flow path connected to an end of liquid reagent measurement portion 106a closer to an outlet thereof and is thus accommodated in drainage reservoir 109a.

Then the separated blood plasma in blood plasma separation portion 103 is introduced by rightward centrifugal force into specimen measurement portion 104 and measured. Blood plasma spilling over specimen measurement portion 104 flows through a flow path connected to an end of specimen measurement portion 104 closer to an outlet thereof and is thus accommodated in a drainage reservoir 109b. Liquid reagent X measured moves to mixer portion 107b and a liquid reagent Y in liquid reagent reservoir portion 105b is output from liquid reagent reservoir portion 105b.

Then, downward centrifugal force is applied to move the measured blood plasma and the measured liquid reagent X to mixer portion 107a to mix them together. Liquid reagent Y is introduced into liquid reagent measurement portion 106b and measured. Liquid reagent Y spilling over liquid reagent measurement portion 106b flows through a flow path connected to an end of liquid reagent measurement portion 106b closer to an outlet thereof and is thus accommodated in a drainage reservoir 109c. Then, rightward, downward, and rightward centrifugal forces are successively applied to move the liquid mixture of the blood plasma and liquid reagent X back and forth between mixer portions 107a and 107b to sufficiently mix the liquid mixture.

Then, upward centrifugal force is applied to mix the liquid mixture of the blood plasma and liquid reagent X, and the measured liquid reagent Y together in mixer portion 107c. Then, leftward, upward, leftward, and upward centrifugal forces are successively applied to move the liquid mixture back and forth between mixer portions 107c and 107d to sufficiently mix the liquid mixture. Finally, rightward centrifugal force is applied to introduce the liquid mixture in mixer portion 107c into detection portion 108. Detection portion 108 accommodates the liquid mixture therein, which is provided for example for optical measurement as described above, and tested and analyzed.

EXAMPLES

Hereinafter the present invention will more specifically be described with reference to examples, although the present invention is not limited thereto.

Example 1

First substrate 101 having step 205, which is a transparent substrate formed of polystyrene resin and having a groove pattern as shown in FIG. 1, and second substrate 301, which is a black substrate formed of resin of polystyrene with powdery carbon mixed therewith together, as shown in FIG. 3, are prepared. Herein, step 205 has depth L1 of 0.15 mm, optical path 201 is defined by a groove having depth L2 of 1.2 mm, and step 205 has widthwise length L3 of 0.3 mm. Then, first substrate 101 and second substrate 301 are placed one on the other, and a laser is radiated to first pass through first substrate 101 to melt second substrate 301's surface to be joined to join the substrates together to obtain a microchip. Then the microchip is cut along a cross section as shown in FIG. 3. Then a CCD microscope is used to observe the cross section to measure a distance W measured from an interface of the substrates to a portion of second substrate 301 that is raised most. Such measurement is conducted for 10 microchips. The result is obtained as shown in table 1.

Comparative Example 1

Except that the first substrate is used without step 205, 10 microchips are fabricated, similarly as done in example 1, and observed in cross section to measure distance W. The result is obtained as shown in table 1.

TABLE 1

| | Distance W | |
|---|---|---|
| Nos. | Example 1 | Comparative Example 1 |
| 1 | 0.17 | 0.34 |
| 2 | 0.16 | 0.32 |
| 3 | 0.17 | 0.34 |
| 4 | 0.15 | 0.34 |
| 5 | 0.17 | 0.33 |
| 6 | 0.17 | 0.36 |
| 7 | 0.17 | 0.36 |
| 8 | 0.17 | 0.38 |
| 9 | 0.15 | 0.34 |
| 10 | 0.15 | 0.32 |
| Average | 0.16 | 0.34 |

Although the present invention has been described and illustrated in detail, it is clearly understood that the same is by way of illustration and example only and is not to be taken by way of limitation, the scope of the present invention being interpreted by the terms of the appended claims.

What is claimed is:

1. A microchip formed of a first substrate having a surface with a groove and a second substrate joined together, and having a fluid circuit in a form of a cavity defined by said groove and a surface of said second substrate closer to said first substrate, said fluid circuit including a detection portion having an optical path for transmitting light, the optical path comprising a portion of the groove, said microchip comprising at least one of a step or a recess, wherein the step is adjacent a side surface of the portion of the groove that defines said optical path, the step having a height that is less than a height of the portion of the groove that defines the optical path, the recess being in said second substrate at a position opposite the side surface of the portion of the groove that defines the optical path.

2. The microchip according to claim 1, wherein said first substrate has at least has two steps each of which is adjacent a different side surface of the portion of said groove defining said optical path.

3. The microchip according to claim 2, wherein the side surfaces of the portion of said groove defining said optical path are, respectively, a plane of incidence of said light and a plane of emission of said light.

4. The microchip according to claim 1, wherein said first substrate has said step and said second substrate does not have said recess.

5. The microchip according to claim 1, wherein the portion of said groove defining said optical path has a depth of at least 1 mm and at most 2 mm.

6. The microchip according to claim 1, wherein a portion of said groove defining said step has a depth of at most 0.5 mm.

7. The microchip according to claim 1, wherein a portion of said groove defining said step has a depth of at most 0.1 mm.

8. The microchip according to claim 1, wherein said first substrate is a transparent substrate.

9. The microchip according to claim 1, wherein said second substrate is an opaque substrate.

10. The microchip according to claim 9, wherein said second substrate is a black substrate.

\* \* \* \* \*